United States Patent
Shahinian, Jr.

(10) Patent No.: US 6,572,849 B2
(45) Date of Patent: Jun. 3, 2003

(54) SELF-PRESERVED ANTIBACTERIAL NASAL, INHALABLE, AND TOPICAL OPHTHALMIC PREPARATIONS AND MEDICATIONS

(76) Inventor: Lee Shahinian, Jr., 1506 Country Club Dr., Los Altos, CA (US) 94024

( * ) Notice: Subject to any disclaimer, the term of this patent is extended or adjusted under 35 U.S.C. 154(b) by 0 days.

(21) Appl. No.: 09/961,194

(22) Filed: Sep. 20, 2001

(65) Prior Publication Data

US 2002/0061340 A1 May 23, 2002

Related U.S. Application Data

(60) Provisional application No. 60/234,319, filed on Sep. 20, 2000.

(51) Int. Cl.[7] ........................ A61K 31/74; A01N 25/00
(52) U.S. Cl. ............................. 424/78.04; 424/78.02; 514/912
(58) Field of Search .................. 424/745, 78.04, 424/78.02; 514/912

(56) References Cited

U.S. PATENT DOCUMENTS 5,756,552 A * 5/1998 Takeuchi et al.

* cited by examiner

Primary Examiner—Christopher R. Tate
Assistant Examiner—Randall Winston
(74) Attorney, Agent, or Firm—Hana Verny

(57) ABSTRACT

Self-preserved nasal, inhalable and topical ophthalmic preparations and medications which destroy, inhibit or therapeutically significantly limit microbial growth within said preparations or medications. The nasal, inhalable, and topical ophthalmic preparations and medications are mildly buffered and maintain a stable pH at pH 3.5 or lower.

15 Claims, No Drawings

SELF-PRESERVED ANTIBACTERIAL NASAL, INHALABLE, AND TOPICAL OPHTHALMIC PREPARATIONS AND MEDICATIONS

This application is based on and claims priority of the Provisional application Ser. No. 60/234,319, filed on Sep. 20, 2000.

FIELD OF THE INVENTION

The current invention concerns buffered, low pH, self-preserved nasal, inhalable and topical ophthalmic preparations and medications which destroy, inhibit or sufficiently limit microbial growth within said preparations or medications. In particular, the current invention involves nasal, inhalable and topical ophthalmic preparations and medications having low pH of about 3.5 or lower, to inhibit microbial growth, wherein immediately upon application to the eye surface or a mucosal surface, the pH rises to physiologic levels.

BACKGROUND OF THE INVENTION

To prevent infection with use, currently available multidose preparations and medications are sterilized during manufacture and have a variety of preservatives added to destroy or inhibit the growth of microorganisms inadvertently introduced into the product after opening.

It is well recognized that the preservatives used in topical ophthalmic medications and preparations can be toxic to the eye surface and respiratory mucosa. The most widely used ophthalmic preservative, benzalkonium chloride (BAK), can cause damage to the conjunctival and corneal epithelium (*Cornea*, 1:221–225 (1992); *Arch Opthalmol*, 110:528–532 (1992) and *CLAO J*, 18:260–266 (1992)). BAK is now thought to be also a significant cause of rhinitis medicamentosa, as described in *Allergy*, 52:627–632 (1997), and has been also shown to damage respiratory mucosa (*Am Rev Respir Dis*, 141:1405–1408 (1990) and *Acta Otolaryngol*, 116:868–875 (1996)). Reducing the concentration of BAK reduces its toxic effect, but at too low a concentration, BAK is no longer effective as a preservative. Although alternatives to BAK are available, all preservatives have some potential for toxicity.

Pressurized aerosol containers used for inhalation or as a spray are an exception, needing no preservative since no air or contamination enters the container as doses are extracted. However, such packaging is relatively bulky and expensive, often contains CFC propellants which can harm the atmosphere, and precludes drop administration.

In recent years, preparations and medications have been packaged in unit-dose containers, thus avoiding the need for potentially toxic preservatives. In this arrangement, a single dose of medicine is provided by a given container. With sterile packaging, microbial contamination is theoretically not a concern, since the consumer/patient is instructed to discard the container after each single use. However, there are several problems with unit dose containers. First, the packaging is bulky and inconvenient. Second, cost per dose is significantly higher than with multidose containers. Third, patients often retain the opened container for many hours or even more than one day, contradicting the package instructions. This pattern of use increases the probability of microbial contamination of the medication or preparation.

Thus, it would be desirable to have available preservative-free preparations and medications suitable for topical, mucosal and inhalation use that could be stored in multidose containers without risk of microbial contamination.

All patents, patent applications and publications are hereby incorporated by reference.

SUMMARY OF THE INVENTION

One aspect of the current invention is a topical ophthalmic, nasal, or inhalable preparation or medication which is self-preserved, that is, which destroys, inhibits or sufficiently limits growth and multiplication of various microorganisms without the addition of preservative agents.

Another aspect of the current invention is a mildly buffered, topical ophthalmic, nasal, or inhalable preparation which is self-preserved by having a pH of from about 1.5 to about 3.5 with preferred pH at about 2.5 or lower.

Another aspect of the current invention is a self-preserved topical ophthalmic, nasal, or inhalable preparation or medication comprising a pharmaceutically acceptable excipient or additive selected from the group consisting of dextrose, polyethylene glycol (PEG), hydroxypropyl methylcellulose (HPMC), sodium chloride, potassium chloride, calcium chloride, magnesium chloride, phosphoric acid, disodium edetate, bicarbonate, phosphate, povidone, carboxymethylcellulose, hydroxyethylcellulose, methylcellulose, microcrystalline cellulose, glycerin, polyvinyl alcohol, dextran 40, dextran 70, mannitol, gelatin, polyol, polysorbate 80, propylene glycol, zinc sulfate, poloxamer 188, 282, 407, ephedrine hydrochloride, naphazoline hydrochloride, oxymetazoline hydrochloride, phenylephrine hydrochloride, tetrahydrozoline hydrochloride, xylometazoline hydrochloride, lecithin, oleic acid, sorbitan, pheniramine maleate, pyrilamine maleate, antazoline phosphate, glycine, camphor, eucalyptol, menthol, benzyl alcohol, lavender oil, tyloxapol, bornyl acetate, and phenylethyl alcohol, and a buffering agent, said preparation or medication adjusted to a low pH between about 1.5 to about pH 3.5, with most preferred pH at about pH 2.5 or lower, said medication optionally containing analgesics, anti-inflammatories, mast cell stabilizers, diagnostic aids, antibiotics, antiglaucoma drugs, decongestants, bronchodilators, vasoconstricting or hypertonicity agents, astringents and topical anesthetics.

Still another aspect of the current invention is a physiologically compatible self-preserved lightly buffered topical ophthalmic, nasal, or inhalable preparation or medication containing no preservation agents, formulated and maintained at about pH 2.5 or lower, wherein immediately upon application to the eye or a mucosal surface, such preparation permits the pH to rise to physiologic levels to maintain patient comfort, prevent tissue damage, and enhance drug delivery.

Still yet another aspect of the current invention is a multidose topical ophthalmic, nasal, or inhalable preparation or medication lightly buffered to maintain a stable pH in the multidose container, thereby maintaining its self-preserving characteristic.

Still another aspect of the current invention is a method for preparation of a topical ophthalmic, nasal or inhalable self-preserved solution comprising steps of:

a) preparing a formulation comprising a pharmaceutically acceptable excipient or additive selected from the group consisting of dextrose, polyethylene glycol (PEG), hydroxypropyl methylcellulose (HPMC), sodium chloride, potassium chloride, calcium chloride, magnesium chloride, phosphoric acid, disodium edetate, bicarbonate, phosphate, povidone, carboxymethylcellulose, hydroxyethylcellulose, methylcellulose, microcrystalline cellulose, other cellulose derivatives, glycerin, polyvinyl alcohol, dextran 40, dextran 70, mannitol, gelatin, polyols, polysorbate 80, propylene glycol, zinc sulfate, poloxamer 188, 282, 407, ephedrine hydrochloride, naphazoline hydrochloride, oxymetazoline hydrochloride, phenylephrine hydrochloride, tetrahydrozoline hydrochloride, xylometazoline hydrochloride, lecithin, oleic acid and sorbitan, pheniramine maleate, pyrilamine maleate, antazoline phosphate, glycine, camphor, eucalyptol, menthol, benzyl alcohol, lavender oil, tyloxapol, bornyl acetate, phenylethyl alcohol, alone or in admixture; and a buffering agent; and b) adjusting pH of said formulation to from about pH 1.5 to pH about 3.5.

DEFINITIONS

As used herein:

"Preparation" means a topical ophthalmic, nasal, or inhalable preparations, including topical eye preparations such as artificial tears, contact lens solutions and eye irrigating solutions; nasal preparations such as saline; and inhalable preparations.

"Medication" means topical ophthalmic, nasal, or inhalable preparations comprising a pharmaceutical agent suitable for topical ophthalmic, nasal or inhalable administration wherein the pharmaceutical agent for ophthalmic use is an astringent, analgesic, hypertonicity agent, antihistamine, anti-inflammatory drug, mast cell stabilizer, diagnostic aid, anesthetic, antibiotic, antiglaucoma drug and vasoconstricting agent, the agent for nasal use is a decongestant and the agent for inhalable use is a bronchodilator "Physiologically compatible" means a preparation or medication which contains pharmaceutically acceptable excipients and additives dissolved or suspended in purified water which is physiologically compatible with the eye surface or the nasal/respiratory mucosa.

"Preservative" means an additive intended to destroy or limit growth and multiplication of microorganisms.

"Self-preserved" means a preservative-free preparation or medication that destroys or inhibits microbial growth without the addition of preservatives such as benzalkonium chloride (BAK).

"Preservative effectiveness testing" or "PET" means the standardized microbiological testing specified by the USP 24 to determine preservative effectiveness.

DETAILED DESCRIPTION OF THE INVENTION

This invention is based on the finding that certain pharmaceutical preparations and medications, when adjusted and maintained at a low pH of from about pH 1.5 to about pH 3.5, are self-preserved and possess antimicrobial growth properties.

The invention, therefore, concerns buffered, low pH, topical self-preserved ophthalmic, nasal, or inhalable preparations or medications for multidose administration of various drugs and pharmaceuticals topically or by inhalation. These preparations or medications generally comprise one or more pharmaceutically acceptable excipients or additives, such as, for example, dextrose, polyethylene glycol (PEG), hydroxypropyl methylcellulose (HPMC), sodium chloride, potassium chloride, calcium chloride, magnesium chloride, phosphoric acid, disodium edetate, bicarbonate, phosphate, povidone, carboxymethylcellulose, hydroxyethylcellulose, methylcellulose, microcrystalline cellulose, other cellulose derivatives, glycerin, polyvinyl alcohol, dextran 40, dextran 70, mannitol, gelatin, polyols, polysorbate 80, propylene glycol, zinc sulfate, poloxamer 188, 282, 407, ephedrine hydrochloride, naphazoline hydrochloride, oxymetazoline hydrochloride, phenylephrine hydrochloride, tetrahydrozoline hydrochloride, xylometazoline hydrochloride, lecithin, oleic acid and sorbitan, pheniramine maleate, pyrilamine maleate, antazoline phosphate, glycine, camphor, eucalyptol, menthol, benzyl alcohol, lavender oil, tyloxapol, bornyl acetate, phenylethyl alcohol, analgesics, anti-inflammatories, mast cell stabilizers, diagnostic aids, antibiotics, antiglaucoma medications, and topical anesthetics, and a buffering agent, said preparation or medication adjusted to a low pH between about 1.5 to about pH 3.5, with the most preferred pH at about pH 2.5 or lower. These preservations and medications are self-preserved by means of low pH.

The invention is based on observations made during studies performed to determine the stability of amino ester topical anesthetics wherein microbial growth was observed to be moderately inhibited by diluted solutions of these topical anesthetics when the solutions were formulated at pH 3.5 to enhance the anesthetic's stability. A further series of experiments discovered and demonstrated that microbial growth is still somehow inhibited at this pH (3.5) even if the anesthetic is removed. These studies, described in greater detail below, showed that for adequate destruction, inhibition or sufficient limitation of microbial growth to meet preservative effectiveness testing (PET) standards, the pH should be not much higher than approximately 2.5 up to pH 3.5 at most.

Moreover, it was further discovered that with appropriate mild or moderate buffering, these preparations or medications may be advantageously administered to the eye surface or to the nasal or respiratory mucosa without a harmful effect caused by such low pH because the mild buffer, under these conditions, permits instant adjustment of the pH to physiologic levels upon administration to the eye topically or to nasal or respiratory mucosa.

The invention, therefore, in its broadest aspect, concerns the discovery that the self-preserved properties of the topical ophthalmic, nasal or inhalable preparation or medication can be achieved with a mild buffering and with maintenance of low pH under 3.5, preferably pH about 2.5 or lower and that this preparation or medication can be advantageously administered to the eye surface or to the nasal or respiratory mucosa without causing irritation or injury.

I. Preservative Effectiveness Testing

In order to determine the optimal composition and pH of the self-preserved preparation, various combinations of components and variable pH were tested using preservative effectiveness testing (PET).

PET procedure, description of which can be found in USP 24, §51, pp.1809–1811, Antimicrobial Effectiveness Testing, was first performed on the following solutions formulated at pH values from 2.5 to 6.5.

Solutions Group A

Solution A consisted of the following components:

| | |
|---|---|
| Dextrose | 0–4.0% |
| Polyethylene Glycol 400 | 0.001–8.0 |
| Hydroxypropyl methylcellulose | 0.30 |
| Edetate Disodium | 0–0.02 |
| Sodium Citrate | 0.01–0.05 |
| Purified Water | QS |
| pH adjusted from 2.5 to 6.5 | |

At pH 5.5 to 6.5, there was inadequate inhibition of microbial growth. At pH 4.5 to 5.5, inhibition of microbial growth did not meet PET standards. At pH 3.5 to 4.5 the inhibition of microbial growth was inconsistent. At pH 2.5 to 3.5, the inhibition of microbial growth met the PET standards. This was still true as the percentages of dextrose, PEG 400, and edetate disodium were varied as shown above. However, inhibition of microbial growth improved as the pH approached 2.5.

Solutions Group B

The above testing clearly indicated that the solutions in Group A having pH above approximately 3.5 did not sufficiently inhibit microbial growth and the best inhibition was seen at pH 2.5. Consequently, two solutions were subjected to further studies performed at pH of about 2.5. However, to reach and maintain the pH at 2.5 using a sodium citrate buffer was found to be difficult. Citric acid was, therefore, used to replace sodium citrate in the low pH solutions to achieve a stable pH 2.5 for long periods of time.

The following two representative formulations, Solutions 1 and 2, both adjusted to pH 2.5, show excellent inhibition of microbial growth and pH stability.

Group B. Solution 1

| | |
|---|---|
| Polyethylene glycal 400 | 8.00% |
| Hydroxypropyl methylcellulose 2910 | 0.30 |
| Citric acid | 0.01 |
| Purified water | QS |
| pH 2.5 | |

Group B. Solution 2

| | |
|---|---|
| Dextrose | 4.00% |
| Polyethylene glycol 400 | 1.00 |
| Hydroxypropyl methylcellulose 2910 | 0.30 |
| Citric acid | 0.01 |
| Purified water | QS |
| pH 2.5 | |

Both solutions were again tested by the PET procedure.

Results of these testings on five types of microorganisms are described below in Tables 1–4. The results seen in Tables 1–4 clearly show that when the solution comprising a viscosity and/or tonicity agent, here represented by polyethylene glycol, dextrose and hydroxypropyl methylcellulose, and a buffering agent, here represented by citric acid, is adjusted to around pH 2.5, it possesses a definite ability to inhibit microbial growth. Both solutions are also able to maintain this pH (2.5) for at least two months or longer at 40° C., and therefore, they have a good stability and long shelf-life.

II. Low pH, Self-Preserved Preparations and Medications

The preparations and medications of the invention are formulated as a solution or suspension comprising components in percentages shown in the Group A solutions, described above. The pH of the invention is optimally about 2.5 or lower. This is in contrast to the physiologic pH of 7.4, typically used for these types of formulations.

The only disclosed use for low pH is a preservative-free beverage composition with pH 2.2–2.7 described in U.S. Pat. No. 5,417,994.

Self-preserved, pharmaceutically acceptable preparations or medications for topical use utilizing pH 2.5 or below have not been previously described or suggested and such self-preserved low pH preparation or medication for topical ophthalmic, mucosal or inhalable administration are not available.

In practice of the current invention, the pH is adjusted to approximately 2.5 with an acid such as hydrochloric or sulphuric acid or a base such as sodium or ammonium hydroxide. Citric acid, acetic, formic, glutaric, glycolic, lactic, maleic, tartaric acid or other weak acid or a salt thereof, such as sodium citrate, may be used to buffer the preparation or medication. Citric acid is the preferred component for a buffer. It has been discovered as part of the current invention that the desirable concentration of citric acid is approximately 0.01%, to lightly buffer the preparation and allow the pH to rise rapidly when the preparation is applied to the tissue surface.

The function of low pH is very important from the point of view of this invention. It is well known that certain drug solutions are unstable when formulated at or near physiologic pH. For example, pilocarpine is relatively unstable at pH 6.8, but very stable at pH 5.0. The concept of lightly buffering such formulations to make them physiologically compatible despite the low pH used for drug stability has been previously known. However, using very low pH such as pH 2.5 or lower with a preparation or medication for any purpose, and more specifically for the purpose of self-preservation of multidose preparations or medications, has not been previously described.

The preparations described herein contain and may additionally contain and be freely exchangeable with any pharmaceutically acceptable excipient or additive, such as for example, dextrose, polyethylene glycol (PEG), hydroxypropyl methylcellulose (HPMC), sodium chloride, potassium chloride, calcium chloride, magnesium chloride, phosphoric acid, disodium edetate, bicarbonate, phosphate, povidone, carboxymethylcellulose, hydroxyethylcellulose, methylcellulose, microcrystalline cellulose, other cellulose derivatives, glycerin, polyvinyl alcohol, dextran 40, dextran 70, mannitol, gelatin, polyols, polysorbate 80, propylene glycol, zinc sulfate, poloxamer 188, 282, 407, ephedrine hydrochloride, naphazoline hydrochloride, oxymetazoline hydrochloride, phenylephrine hydrochloride, tetrahydrozoline hydrochloride, xylometazoline hydrochloride, lecithin, oleic acid and sorbitan, pheniramine maleate, pyrilamine maleate, antazoline phosphate, glycine, camphor, eucalyptol, menthol, benzyl alcohol, lavender oil, tyloxapol, bornyl acetate, phenylethyl alcohol, and other excipients and additives which are pharmaceutically acceptable.

These excipients and additives are dissolved or suspended in sterile distilled or sterile purified water up to the volumes to provide a solution or suspension containing these components in the desired ratios to each other.

Additionally, the preparations described herein are advantageously formulated into medications by combining said excipient with pharmaceutical agents, such as analgesics, anti-inflammatories, antihistamines, mast cell stabilizers, diagnostic aids, such as fluorescein, anesthetic solutions, miotics, mydriatics, antibiotics, antivirals, antifungals, anti-glaucoma drugs, hypertonic agents, astringents, and local anesthetics such as proparacaine, tetracaine, lidocaine, benoxinate, and bupivicaine, etc., and such other therapeutic agents which are typically used for administration to the eye surface and nasal or respiratory mucosa. These pharmaceutical agents are present in from about 0.001% to about 8%.

These solutions are suitable for use as artificial tears and as solution for administration of various drugs and pharmaceuticals as well as washing solution for contact lenses. The solutions are self-preserved without the addition of any preservative agent. Additionally, when administered to the eye, or other mucosal surface, these solutions permit rapid adjustment of pH to the physiologic levels.

For artificial tears, the formulation comprises from about 0.001 to about 8% of one or two or more viscosity and/or tonicity-providing agents, and from about 0.005 to about 0.02%, preferably above 0.01% of a mild buffering agent. The above components are dissolved in purified water up to 100% and pH is appropriately adjusted with an acid or a base to levels lower than pH 3.5. The percentage of the agents can be increased or decreased to vary the tonicity as desired. For example, the eye can usually tolerate solutions with tonicity equivalent to that provided by 0.5% to 1.8% sodium chloride.

III. Testing of Representative Embodiments

One representative embodiment for an ophthalmic demulcent (artificial tear) is a formulation designated solution 1 which comprises about 8% of polyethylene glycol 400 (PEG 400), about 0.3% of HPMC 2910 and about 0.01% of citric acid dissolved in 100 ml of purified water and adjusted to about pH 2.5.

This formulation has been shown to significantly inhibit the growth of microorganisms, such as $P.$ aeruginosa, $E.$ coli, $S.$ aureus, $C.$ albicans and $A.$ niger for at least 28 days, as seen in Table 1. In this formulation, PEG 400 provides tonicity and viscosity. The HPMC provides viscosity, and the citric acid lightly buffers the preparation.

TABLE 1

Preservative Effectiveness Testing for Solution 1

| Organism | Initial | 6 Hours | 24 Hours | 7 Days | 14 Days | 21 Days | 28 days |
|---|---|---|---|---|---|---|---|
| P. aeruginosa | $4.8 \times 10^5$ | <100 | <100 | <1 | <1 | <1 | <1 |
| Saline | $1.6 \times 10^6$ | $5.6 \times 10^5$ | $5.8 \times 10^5$ | $7.8 \times 10^5$ | $3.4 \times 10^5$ | $6.4 \times 10^5$ | $6.0 \times 10^5$ |
| E. coli | $2.8 \times 10^5$ | $1.6 \times 10^4$ | <1000 | <1 | <1 | <1 | <1 |
| Saline | $4.1 \times 10^6$ | $2.6 \times 10^6$ | $3.4 \times 10^6$ | $2.7 \times 10^6$ | $1.7 \times 10^6$ | $2.0 \times 10^6$ | $2.6 \times 10^6$ |
| S. aureus | $2.0 \times 10^6$ | $1.4 \times 10^5$ | <1000 | <1 | <1 | <1 | <1 |
| Saline | $3.9 \times 10^5$ | $2.2 \times 10^6$ | $1.3 \times 10^6$ | $1.0 \times 10^5$ | $3.0 \times 10^3$ | <1000 | 16 |
| C. albicans | $1.4 \times 10^6$ | Not Done | $4.5 \times 10^5$ | $6.0 \times 10^2$ | $6.6 \times 10^1$ | $5.5 \times 10^1$ | 5 |
| Saline | $1.7 \times 10^6$ | Not Done | $8.4 \times 10^5$ | $4.8 \times 10^5$ | $2.9 \times 10^5$ | $2.9 \times 10^5$ | $1.4 \times 10^5$ |
| A. niger | $6.1 \times 10^4$ | $5.0 \times 10^4$ | $1.9 \times 10^4$ | $3.1 \times 10^4$ | $1.9 \times 10^4$ | $2.2 \times 10^4$ | $1.1 \times 10^4$ |
| Saline | $2.8 \times 10^5$ | $1.7 \times 10^5$ | $1.4 \times 10^5$ | $5.0 \times 10^4$ | $3.3 \times 10^4$ | $8.0 \times 10^4$ | $1.4 \times 10^4$ |

Table 1 shows that the concentration in colony forming units (CFU)/ml for the three bacterial organisms inoculated in Solution 1 decreased by greater than 3 logs at 14 days and remained at that level for 28 days, thus meeting the PET requirements.

Both $C.$ albicans and $A.$ niger met or exceeded the PET requirement for yeasts and molds to remain at or below the initial concentration.

TABLE 2

PH Testing for Solution 1

| | Day 1 | Day 7 | Day 14 | Day 21 | Day 28 |
|---|---|---|---|---|---|
| P. aeruginosa | 2.43 | 2.36 | 2.44 | 2.41 | 2.40 |
| E. coli | 2.45 | 2.37 | 2.45 | 2.41 | 2.37 |
| S. aureus | 2.41 | 2.36 | 2.44 | 2.41 | 2.38 |
| C. albicans | 2.42 | 2.41 | 2.45 | 2.43 | 2.42 |
| A. niger | 2.42 | 2.40 | 2.39 | 2.35 | 2.35 |

As seen in Table 2, Solution 1 maintained its pH close to its original pH value 2.5 for at least 28 days in the presence of all tested organisms.

Solution 1 was also pH stable when incubated at 40° C. for greater than two months.

Another representative embodiment for an artificial demulcent is a formulation designated solution 2, which comprises 4% of dextrose, 1% of PEG 400, 0.3% of hydroxypropylmethyl cellulose 2910 and 0.01% of citric acid, dissolved in 100 ml of purified water and pH adjusted to 2.5. In this solution, the dextrose and PEG 400 both serve as tonicity agents. This formulation, designated as Solution 2, has been tested similarly to Solution 1. Results are seen in Table 3.

TABLE 3

Preservative Effectiveness Testing for Solution 2

| Organism | Initial | 6 Hours | 24 Hours | 7 Days | 14 Days | 21 Days | 28 Days |
|---|---|---|---|---|---|---|---|
| P. aeruginosa | $1.3 \times 10^6$ | $1.8 \times 10^4$ | <100 | <1 | <1 | <1 | <1 |
| Saline | $1.6 \times 10^6$ | $5.6 \times 10^5$ | $5.8 \times 10^5$ | $7.8 \times 10^5$ | $3.4 \times 10^5$ | $6.4 \times 10^5$ | $6.0 \times 10^5$ |
| E. coli | $4.0 \times 10^6$ | $1.6 \times 10^4$ | <1,000 | <1 | <1 | <1 | <1 |
| Saline | $4.1 \times 10^6$ | $2.6 \times 10^6$ | $3.4 \times 10^6$ | $2.7 \times 10^6$ | $1.7 \times 10^6$ | $2.0 \times 10^6$ | $2.6 \times 10^6$ |
| S. aureus | $1.5 \times 10^6$ | $2.0 \times 10^5$ | <1,000 | <1 | <1 | <1 | <1 |
| Saline | $3.9 \times 10^6$ | $2.2 \times 10^6$ | $1.3 \times 10^6$ | $1.0 \times 10^5$ | $3.0 \times 10^3$ | <1,000 | 16 |
| C. albicans | $1.9 \times 10^6$ | N/A | $8.6 \times 10^5$ | $1.7 \times 10^5$ | $2.0 \times 10^4$ | $5.8 \times 10^2$ | 17 |
| Saline | $1.7 \times 10^6$ | N/A | $8.4 \times 10^5$ | $4.8 \times 10^5$ | $2.6 \times 10^5$ | $2.9 \times 10^5$ | $1.4 \times 10^5$ |
| A. niger | $7.8 \times 10^4$ | $1.9 \times 10^4$ | $1.4 \times 10^4$ | $2.7 \times 10^4$ | $2.4 \times 10^4$ | $1.5 \times 10^4$ | $1.0 \times 10^4$ |
| Saline | $2.8 \times 10^5$ | $1.7 \times 10^5$ | $1.4 \times 10^5$ | $5.0 \times 10^4$ | $3.3 \times 10^4$ | $8.0 \times 10^4$ | $1.4 \times 10^4$ |

Table 3 shows that Solution 2 was also able to meet or exceed the PET standards for inhibition of the growth of all tested microorganisms over the 28 day test.

TABLE 4 pH Testing for Solution 2

| | Day 1 | Day 7 | Day 14 | Day 21 | Day 28 |
|---|---|---|---|---|---|
| P. aeruginosa | 2.42 | 2.32 | 2.41 | 2.41 | 2.40 |
| E. coli | 2.41 | 2.30 | 2.41 | 2.40 | 2.37 |
| S. aureus | 2.43 | 2.32 | 2.41 | 2.39 | 2.38 |
| C. albicans | 2.40 | 2.41 | 2.41 | 2.40 | 2.36 |
| A. niger | 2.40 | 2.40 | 2.33 | 2.25 | 2.08 |

Solution 2 was also able to maintain a stable pH of around 2.0 to 2.5 for at least 28 days in the presence of all tested organisms, as seen in Table 4, and for up to three months when incubated at 40° C.

These findings clearly show that the solutions of the invention are able to destroy, inhibit and therapeutically significantly limit the microbial growth when the pH is maintained at pH about pH 2.5 or lower.

All excipients and additives, alone or in varieties of combinations, in percentages as disclosed, with or without the presence of a pharmaceutical agent, are intended to be within the scope of this invention as long as they are formulated and maintained at pH lower than 3.5.

EXAMPLE 1

Artificial Tears Formulation

This example describes preparation and testing of Solutions 1 and 2.

One formulation of the invention was prepared for artificial tears. The formulation consists of polyethylene glycol 400 (PEG 400) 8%, HPMC 0.3%, citric acid 0.01%, and purified water QS, with pH adjusted to 2.5 with hydrochloric acid.

This formulation was instilled in one eye of ten subjects. The other eye was treated with Genteal, a commercially available artificial tear. The formulation drops were consistently at least as comfortable as Genteal, administered in the fellow eye. There was variable slight to moderate stinging in most subjects if the citric acid concentration was increased to 0.02 or 0.03%. Therefore, approximately 0.01% is the maximum desired citric acid concentration for comfort.

The same formulation was used in a further pilot clinical experiment to test safety. Following baseline slit lamp examination, one drop of the formulation was placed in the right eye of the subject every 15 minutes for eight hours. The left eye was similarly treated with Genteal artificial tears as a control. Drop instillation was completely comfortable in both eyes. Follow-up slit lamp examination revealed no corneal fluorescein staining in either eye. The same formulation and control solution were used in a similar manner in one subject wearing soft contact lenses. Again, drop instillation was comfortable in both eyes, and no corneal fluorescein staining was seen on follow-up examination.

In a further clinical experiment, a nasal spray bottle was filled with the preparation of Solution 1. It was repeatedly sprayed into the right and left nostril of the subject. No irritation or unpleasant sensation was noted on either side.

Another formulation of the invention for artificial tears consists of dextrose 4.0%, PEG 400 1.0%, HPMC 0.3%, citric acid 0.01%, and purified water OS, with the pH adjusted to 2.5 with hydrochloric acid. In this formulation, dextrose is the main tonicity agent. Similar molecules such as mannitol, or electrolytes such as sodium chloride, can also be used to adjust the tonicity. This formulation, described above as Solution 2, was tested in the same manner as Solution 1.

EXAMPLE 2

Preparation of Solutions 1 and 2

This example describes a procedure used for preparation of Solutions 1 and 2 and with moderate modifications is suitable for preparation of all combinations of various excipients and/or additives and pharmaceutical agents and salts thereof.

Solutions were prepared as follows:

All of the solutions were prepared using Class A volumetric flasks and pipettes. Test solutions were prepared on weight basis, except for the pH adjustments which were made volumetrically. One (1) liter of each test solution was made.

The hydroxypropyl methylcellulose was weighed out and mixed into 500 mL of cold de-ionized water (4° C.). The solution was mixed using a stir bar and stir plated until the cellulose dissolved completely. The rest of the ingredients were then added in the following order: polyethylene glycol, citric acid, glucose (if used), another 400 mL of de-ionized water was added, stirred and adjusted to the correct pH with hydrochloric acid (0.1 N). The solutions were then made up to volume with de-ionized water and allowed to sit overnight. The pH was rechecked and adjusted, if needed, and then filtered through a one (1) liter 0.22 µm polyethersulfone single use filtering system.

EXAMPLE 3

Stability and Storage

This example describes conditions suitable for stability and storage.

The formulations disclosed in Example 1 was stored at 40° C. for more than 2 months for accelerated pH stability testing. The solution was sterilized before storage. The pH was tested weekly for 11 weeks. All samples tested were found to be stable with pH around 2.5 for the 11 weeks.

What is claimed:

1. A self-preserved preservative-free topical ophthalmic, inhalable or nasal formulation comprising:

from about 0.001 to about 8% (w/v) concentration of a pharmaceutically acceptable excipient or additive selected from the group consisting of a pharmaceutically acceptable excipient or additive selected from the group consisting of dextrose, polyethylene glycol (PEG), hydroxypropyl methylcellulose (HPMC), sodium chloride, potassium chloride, calcium chloride, magnesium chloride, phosphoric acid, disodium edetate, bicarbonate, phosphate, povidone, carboxymethylcellulose, hydroxyethylcellulose, methylcellulose, microcrystalline cellulose, other cellulose derivatives, glycerin, polyvinyl alcohol, dextran 40, dextran 70, mannitol, gelatin, polyols, polysorbate 80, propylene glycol, zinc sulfate, poloxamer 188, 282, 407, ephedrine hydrochloride, naphazoline hydrochloride, oxymetazoline hydrochloride, phenylephrine hydrochloride, tetrahydrozoline hydrochloride, xylometazoline hydrochloride, lecithin, oleic acid and sorbitan, pheniramine maleate, pyrilamine maleate, antazoline phosphate, glycine, camphor, eucalyptol, menthol, benzyl alcohol, lavender oil, tyloxapol, bornyl acetate, and phenylethyl alcohol, alone or in admixture; and from about 0.005 to about 0.02% (w/v) concentration of a buffering agent;

said formulation adjusted to a pH from about pH 1.5 to about pH 2.5.

2. The formulation of claim 1 wherein the pH is adjusted to about pH 2.0 to about 2.5.

3. The formulation of claim 2 wherein the pH is about 2.5.

4. The formulation of claim 3 wherein the buffering agent is acetic, citric, formic, glutaric, glycolic, lactic, maleic or tartaric acid or a salt thereof present in concentration from about 0.01 to about 0.02% (w/v).

5. The formulation of claim 4 wherein the buffering agent is citric acid present in concentration of about 0.01% (w/v).

6. The formulation of claim 4 additionally comprising a pharmaceutical agent wherein the pharmaceutical agent is present in from 0.001 to about 8% (w/v) concentration and wherein the buffering agent is present in about 0.01% (w/v) concentration.

7. The formulation of claim 1 comprising about 1–8% (w/v) concentration of polyethylene glycol, about 0.1% to about 0.3% of hydroxypropyl methylcellulose, about 0.01% to about 0.02% citric acid and purified water, wherein the pH is adjusted to about pH 2.5.

8. The formulation of claim 7 comprising about 8% of polyethylene glycol, about 0.3% of hydroxypropyl methylcellulose, about 0.01% citric acid and purified water, wherein the pH is adjusted to about pH 2.5.

9. The formulation of claim 8 wherein the pH is adjusted with an acid or a base.

10. The formulation of claim 9 wherein the acid is hydrochloric acid or sulphuric acid and wherein the base is sodium hydroxide or ammonium hydroxide.

11. The formulation of claim 7 additionally comprising about 2 to 6% of dextrose.

12. The formulation of claim 11 comprising about 4% of dextrose, about 1% of polyethylene glycol, about 0.3% of hydroxypropyl methylcellulose and about 0.01% of citric acid.

13. The formulation of claim 12 wherein the pH is adjusted with an acid or a base.

14. The formulation of claim 13 wherein the acid is hydrochloric acid, phosphoric acid or sulphuric acid and wherein the base is sodium hydroxide or ammonium hydroxide.

15. The formulation of claim 6 wherein the pharmaceutical agent is selected from the group consisting of an analgesic, anti-inflammatory, astringent, antihistamine, mast cell stabilizer, diagnostic aid, fluorescein, miotic, mydriatic, antibiotic, antiviral, antifungal, vasoconstricting agent, anti-glaucoma medication, hypertonicity agent, decongestant, bronchodilator and topical anesthetic.

* * * * *